(12) United States Patent
Kimura et al.

(10) Patent No.: US 8,864,672 B2
(45) Date of Patent: Oct. 21, 2014

(54) BLOOD RHEOLOGY MEASUREMENT DEVICE AND BLOOD RHEOLOGY MEASUREMENT METHOD

(75) Inventors: Fumio Kimura, Chiba (JP); Takahiko Nakamura, Chiba (JP); Masataka Shinogi, Chiba (JP); Mizuaki Suzuki, Chiba (JP)

(73) Assignee: Seiko Instruments Inc. (JP)

( * ) Notice: Subject to any disclaimer, the term of this patent is extended or adjusted under 35 U.S.C. 154(b) by 1620 days.

(21) Appl. No.: 11/350,461

(22) Filed: Feb. 9, 2006

(65) Prior Publication Data

US 2006/0241460 A1    Oct. 26, 2006

(30) Foreign Application Priority Data

Feb. 14, 2005    (JP) .................................. 2005-035885

(51) Int. Cl.
  *A61B 8/00*    (2006.01)
  *A61B 5/02*    (2006.01)
  *A61B 8/08*    (2006.01)
  *A61B 8/06*    (2006.01)

(52) U.S. Cl.
  CPC ............... *A61B 8/00* (2013.01); *A61B 5/02035* (2013.01); *A61B 8/0891* (2013.01); *A61B 8/06* (2013.01); *A61B 8/065* (2013.01)
  USPC ........... 600/454; 600/407; 600/437; 600/453; 600/455; 600/456

(58) Field of Classification Search
  CPC ........ A61B 5/02035; A61B 8/06; A61B 8/00; A61B 8/065; A61B 8/0891
  USPC .................................. 600/407, 437, 453–456
  See application file for complete search history.

(56) References Cited

U.S. PATENT DOCUMENTS

| | | | | | |
|---|---|---|---|---|---|
| 4,554,926 | A | * | 11/1985 | Shirasaka | 600/455 |
| 4,580,574 | A | * | 4/1986 | Gavish | 600/449 |
| 4,611,496 | A | * | 9/1986 | Komachi | 73/861.27 |
| 5,462,057 | A | * | 10/1995 | Hunt et al. | 600/447 |
| 5,501,224 | A | * | 3/1996 | Shiki | 600/456 |
| 7,048,691 | B2 | * | 5/2006 | Miele et al. | 600/504 |
| 7,147,602 | B2 | * | 12/2006 | Muramatsu et al. | 600/504 |
| 2003/0032869 | A1 | * | 2/2003 | Muramatsu et al. | 600/300 |
| 2006/0184026 | A1 | * | 8/2006 | Nakamura et al. | 600/438 |

* cited by examiner

*Primary Examiner* — Tse Chen
*Assistant Examiner* — Vani Gupta
(74) *Attorney, Agent, or Firm* — Adams & Wilks

(57) ABSTRACT

A blood rheology measurement device measures a blood rheology of blood flowing through an artery inside of a living body from outside of the living body. The blood rheology measurement device has a sensor that detects a flow rate of blood flowing through the artery and a pulsatile displacement that varies with an elapse of time. The pulsatile displacement corresponds to a displacement of the artery in a diameter direction thereof due to expansion and contraction of the artery resulting from a pulsatile motion of the heart. A calculating section calculates the blood rheology of blood flowing through the artery on the basis of the blood flow rate and the pulsatile displacement detected by the sensor.

14 Claims, 11 Drawing Sheets

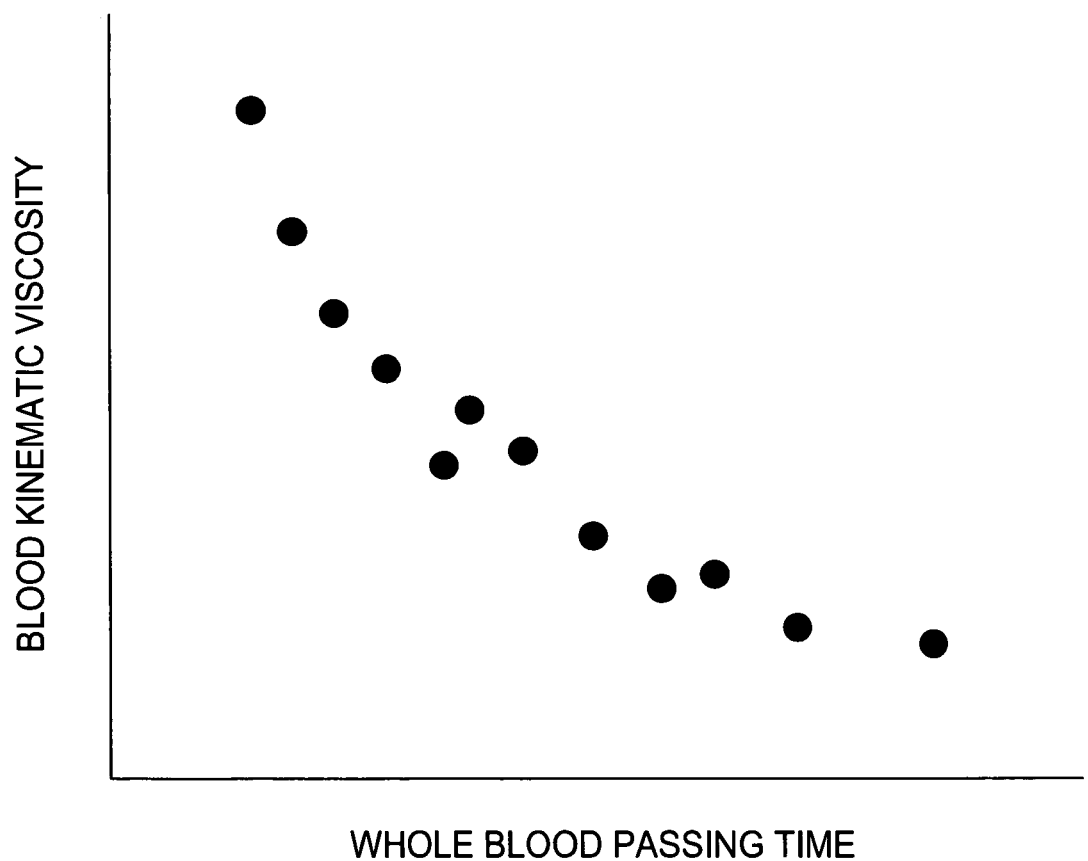

_US 8,864,672 B2_

BLOOD RHEOLOGY MEASUREMENT DEVICE AND BLOOD RHEOLOGY MEASUREMENT METHOD

BACKGROUND OF THE INVENTION

1. Field of the Invention

The present invention relates to measurement device and method of a body fluid circulating in a living body, more particularly to a blood rheology measurement device and a blood rheology measurement method for use in grasping a condition of blood to perform evaluation of health, diagnosis of disease, evaluation of effects of medicine and the like.

2. Description of the Related Art

As one of inspection items for judging a human health condition, there has been noted blood rheology measurement focusing on a fluidity of blood. As means for measuring blood rheology, there is developed a micro channel array type blood fluidity measurement device to measure a time for which a certain amount of blood sampled from a subject passes through a micro channel array (see, e.g., "Measurement of Fluidity of Whole Blood by use of Capillary Blood Vessel Model" by Yuji Kikuchi (Food Research Result Information, No. 11 issued in 1999)). At present, the micro channel array type blood fluidity measurement device is regarded as a standard machine in blood rheology measurement.

However, in the measurement by the micro channel array type blood fluidity measurement device, it is surely necessary to sample the blood. The measurement is performed by a medical institution only, and anyone cannot readily inspect the health condition anywhere. The sampling of the blood imposes a large physical and mental burden on the subject, and a limit of the number of times when the measurement can be performed per day is several times at most. Therefore, there is a problem that data continued in time series cannot be easily obtained.

In addition, it is considered that there is a strong correlation between the blood rheology and a blood flow rate in a living body. That is, it is considered that the blood flow rate is slow at a high viscosity of the blood, and high at a low viscosity. Therefore, the measurement of the blood flow rate in the living body indirectly makes it possible to known the blood rheology (see, e.g., Japanese Patent Application Laid-Open No. 2003-159250).

On the other hand, to calculate an index of the blood rheology on the basis of the blood flow rate in a blood vessel, in addition to the measurement of the blood flow rate, it is necessary to perform measurement of a blood pressure of the living body by use of a cuff as described in Japanese Patent Application Laid-Open No. 2003-159250. As a method of calculating the blood rheology, that is, an index of kinematic viscosity of the blood by use of this blood pressure value and the blood flow rate, there is a method based on a concept that a blood flow pressure in an artery as an object is approximated by means of the blood pressure value.

However, in the method of calculating the blood rheology, that is, the index of the kinematic viscosity of the blood by use of the blood pressure value and the blood flow rate, there is a problem that a measurement error is large because the blood flow pressure in the artery is approximated by means of the blood pressure value. Furthermore, it is essential to miniaturize the device which measures the blood rheology of a portion such as wrist or fingertip, but this is disadvantageously difficult from viewpoints of a mechanism for the blood pressure measurement, intricacy of the mechanism and the like.

Consequently, an object of the present invention is to provide a miniaturized blood rheology measurement device and a blood rheology measurement method which are capable of simply measuring blood rheology of a portion such as wrist or fingertip with a high precision without requiring blood pressure measurement.

SUMMARY OF THE INVENTION

To solve the above-described problem, the present invention is, characterized by: detecting an artery blood flow rate, a pulsatile displacement, an artery diameter, an artery wall thickness, a heartbeat frequency, and a phase difference or an amplitude ratio of the blood flow rate and the pulsatile displacement, which change with elapse of time, by use of a sensor including ultrasonic wave transmitting and receiving elements for transmitting and receiving ultrasonic waves between the surface of a living body and an artery blood flow in the living body; and calculating a blood kinematic viscosity by use of one of the phase difference and the amplitude ratio, the blood vessel diameter, and the heartbeat frequency to obtain an index value of a blood rheology.

FIG. 11 is a characteristic diagram showing effects of the present invention. There is shown a correlation between a kinematic viscosity $\upsilon$ which is an index value of blood rheology calculated from the phase difference of the blood flow rate and the pulsatile displacement measured by the blood rheology device in the present invention and a whole blood passing time T which is an index of blood rheology by a blood sampling system by use of a micro channel array. The ordinate indicates $\upsilon$. In FIG. 11, a value of $\upsilon$ is small close to an origin of the ordinate, and the value of $\upsilon$ is large when ascending the ordinate. As described in detail, the small value of $\upsilon$ means that a viscosity of blood is large.

On the other hand, the abscissa indicates a whole blood passing time T. In FIG. 11, a value of T is small close to the origin of the ordinate, and the value of T is large on the right side. That is, the small value of the whole blood passing time T means that the blood being measured is fluid blood. That is, $\upsilon$ indicates a large value. On the other hand, the large value of the whole blood passing time T means that the blood being measured is viscous blood having a high viscosity. That is, the high viscosity indicates the small value of $\upsilon$. In consideration of these relations, as shown in FIG. 11, it can be considered that there is a significant correlation between $\upsilon$ and the whole blood passing time T.

Therefore, as seen from FIG. 11, the blood rheology measurement device of the present invention is capable of measuring the blood rheology of wrist or fingertip with a good precision without, requiring blood pressure measurement. Therefore, it is possible to supply a simple, high-precision, and miniature blood rheology measurement device. As a result, anyone other than a specialist can readily check rheology correctly without sampling the blood from a subject, and the device is usable in checking a health condition.

BRIEF DESCRIPTION OF THE DRAWINGS

FIG. 11 is a characteristic diagram showing effects of the present invention.

Figure 1:
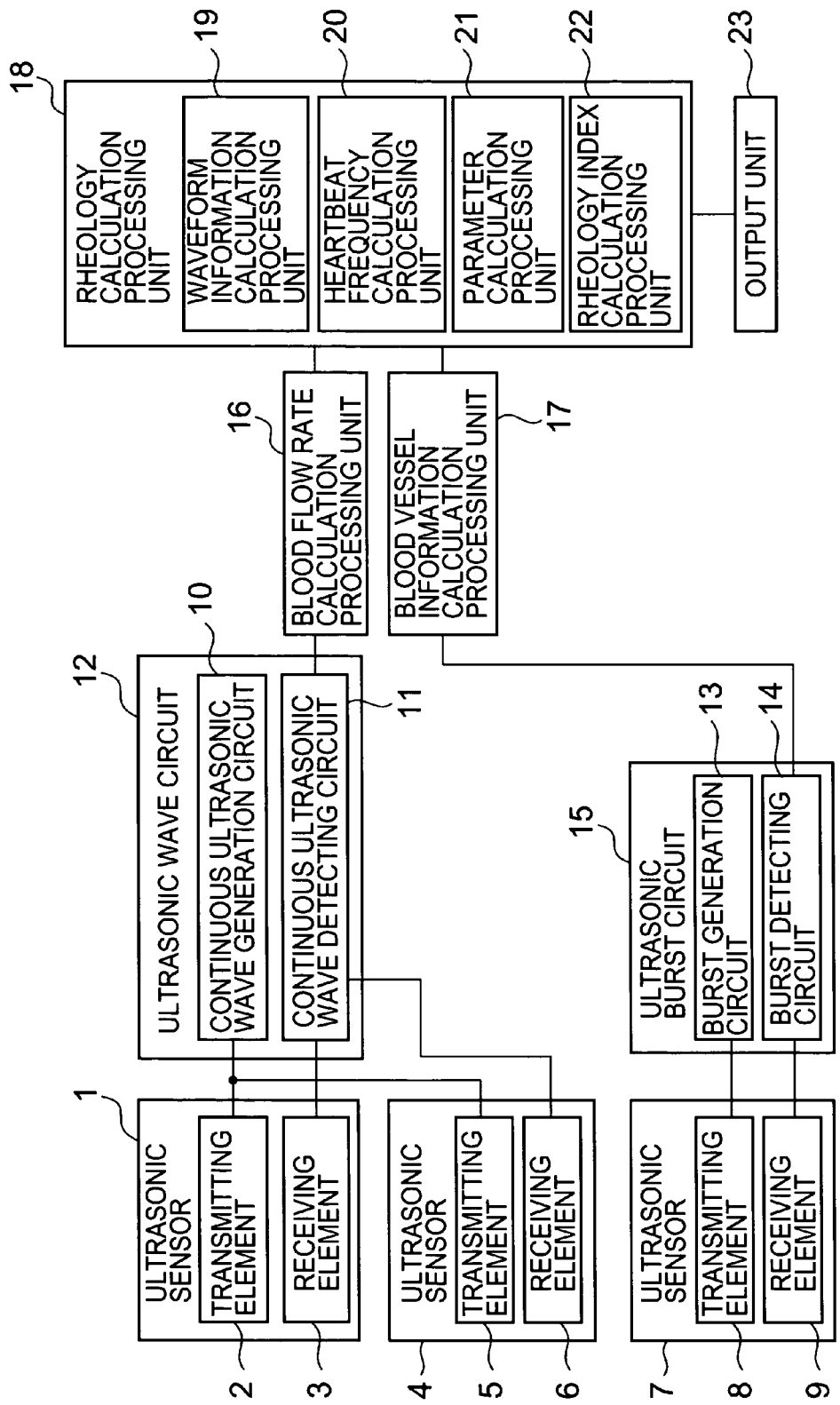
FIG. 1 is a block diagram showing a constitution of a blood rheology measurement device in the present invention.

DESCRIPTION OF REFERENCE NUMERALS 1 ultrasonic sensor
2 transmitting element
3 receiving element
4 ultrasonic sensor
5 transmitting element
6 receiving element
7 ultrasonic sensor
8 transmitting element
9 receiving element
10 continuous ultrasonic wave transmitting circuit
11 continuous ultrasonic wave detecting circuit
12 ultrasonic wave circuit
13 burst generation circuit
14 burst detecting circuit
15 ultrasonic wave burst circuit
16 blood flow rate calculation processing unit
17 blood vessel information calculation processing unit
18 rheology calculation processing unit
19 waveform information calculation processing unit
20 heartbeat calculation processing unit
21 parameter calculation processing unit
22 rheology index calculation processing unit
23 output unit

DESCRIPTION OF THE PREFERRED EMBODIMENT

FIG. 1 shows a block diagram of a constitution of a blood rheology measurement device in the present invention. A sensor unit is constituted of a pair of wave sensors 1 and 4, and an ultrasonic sensor 7 independent of the pair of ultrasonic sensors. The ultrasonic sensor 1 is constituted of a transmitting element 2 and a receiving element 3, the ultrasonic sensor 4 is constituted of a transmitting element 5 and a receiving element 6, and the ultrasonic sensor 7 is constituted of a transmitting element 8 and a receiving element 9. The transmitting elements 2 and 5 are connected to a continuous ultrasonic wave generation circuit 10, an electric signal generated by the continuous ultrasonic wave generation circuit 10 is converted into a mechanical ultrasonic wave, and the ultrasonic wave is transmitted into a living body.

An ultrasonic signal reflected by a blood flow in an artery and involving the Doppler signal is converted into the electric signal by the receiving elements 3 and 6, the signal is input into a continuous ultrasonic wave detecting circuit 11, and the Doppler electric signal is detected. An ultrasonic wave circuit 12 is constituted of two types of circuits which are the continuous ultrasonic wave generation circuit 10 and the continuous ultrasonic wave detecting circuit 11. A burst generation circuit 13 outputs an electric burst signal to the connected transmitting element 8 to drive the transmitting element 8. The transmitting element 8 converts the electric burst signal into an ultrasonic burst signal to emit the ultrasonic burst signal into the living body. The emitted ultrasonic burst signal is reflected by the artery, and converted into the electric signal by the receiving element 9. Thereafter, the signal is input into a burst detecting circuit 14, and the burst ultrasonic wave reflected by the artery is detected as the electric signal in the burst detecting circuit 14. An ultrasonic burst circuit 15 is constituted of two types of circuits which are the burst generation circuit 13 and the burst detecting circuit 14.

The Doppler electric signal detected by the continuous ultrasonic wave detecting circuit 11 includes a blood flow rate signal component which involves a periodic change synchronized with a living body heartbeat. A device for separately extracting the electric signal corresponding to a blood flow rate, that is, a blood flow rate signal from the Doppler electric signal is a blood flow rate calculation processing unit 16. The electric signal corresponding to the reflected burst ultrasonic wave detected by the burst detecting circuit 14 includes artery pulsatile displacement and shape information involving the periodic change synchronized with the living body heartbeat. A device for separately extracting the artery pulsatile displacement and shape information from the electric signal is a blood vessel information calculation processing unit 17.

The blood flow rate signal output from the blood flow rate calculation processing unit 16 and a blood vessel information signal output from the blood vessel information calculation processing unit 17 are input into a rheology calculation processing unit 18 of the present invention. The rheology calculation processing unit 18 is constituted of: a waveform information calculation processing unit 19; a heartbeat frequency calculation processing unit 20; a parameter calculation processing unit 21; and a rheology index calculation processing unit 22. A rheology index detected by the rheology calculation processing unit 18 is output via an output unit 23. As described above, FIG. 1 shows an embodiment in which the ultrasonic sensor unit for measuring the blood flow rate and the ultrasonic sensor for measuring blood vessel information are disposed independently of each other.

Figure 2:
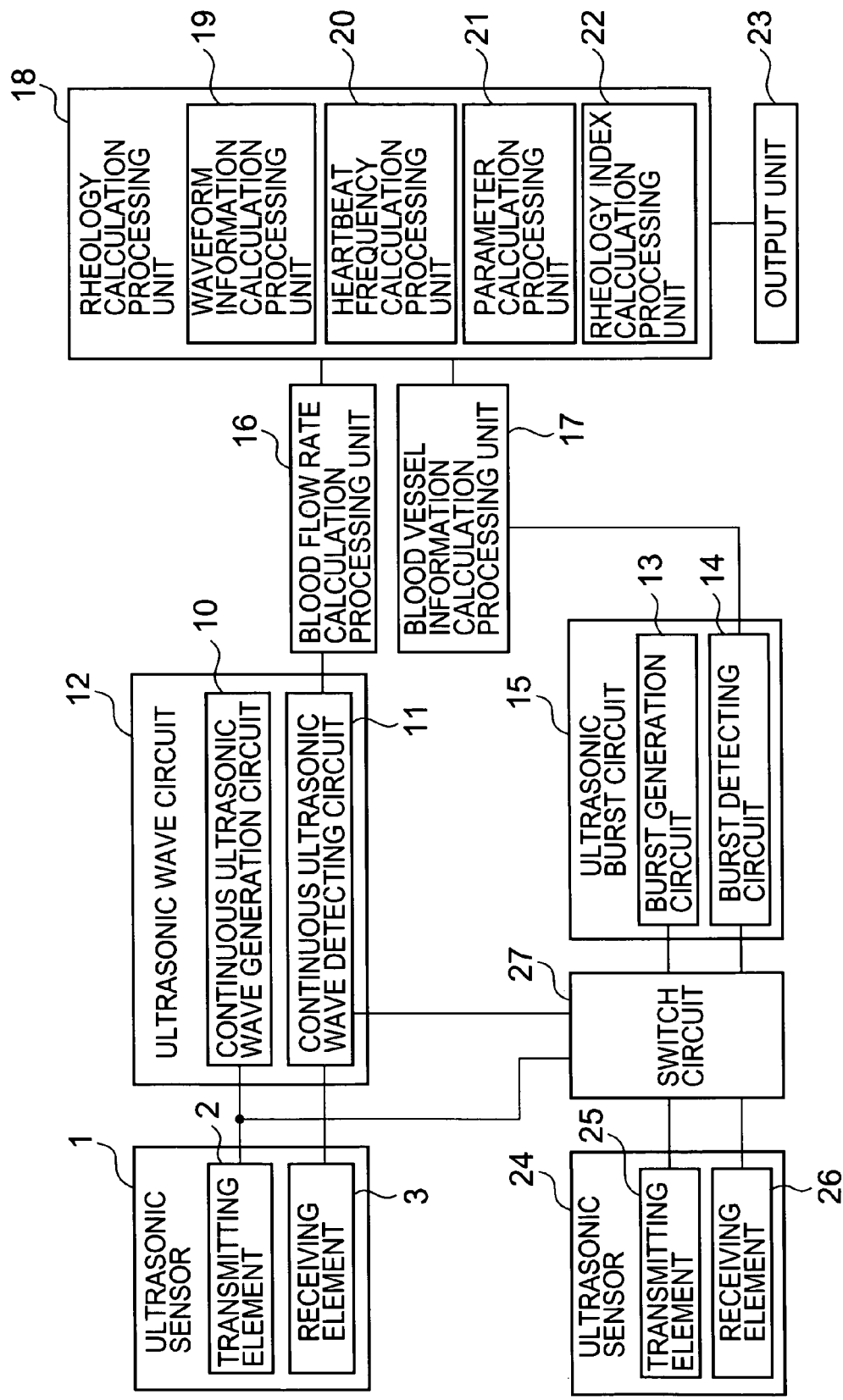
FIG. 2 is a second block diagram showing a constitution of a blood rheology measurement device in the present invention.

FIG. 2 shows a block diagram of a constitution of a second blood rheology measurement device in the present invention. A sensor unit is constituted of a pair of ultrasonic sensors 1 and 24. A transmitting element 25 and a receiving element 26 constituting the ultrasonic sensor 24 are connected to both of an ultrasonic wave circuit 12 and an ultrasonic burst circuit 15 via a switch circuit 27. This switch circuit 27 periodically switches a circuit to be connected to the ultrasonic sensor 24 to the ultrasonic wave circuit 12 or the ultrasonic burst circuit 15.

That is, the ultrasonic sensor 24 comes to have a function of both of blood flow rate detection and blood vessel information detection. A blood flow rate is detected based on measurement of the Doppler deflection amount of an ultrasonic frequency, and blood vessel information is detected based on measurement of a delay time or the like of a reflected burst wave. Therefore, a time width capable of measuring these measurement physical amounts may be set to a switching period of the switch circuit 27 shown in FIG. 2, and this is merely a design matter. FIG. 2 shows an embodiment in which the ultrasonic sensor unit for measuring the blood flow rate also has a sensing function of measuring the blood vessel information.

The embodiments have been described above in which a plurality of ultrasonic sensors for measuring the blood flow rate are used. However, the present invention is not especially limited to the use of the plurality of ultrasonic sensors. For example, one ultrasonic sensor, that is, the only ultrasonic sensor 1 constituted of the transmitting element 2 and the receiving element 3 may be used. However, two ultrasonic sensors are preferably used as in the present embodiment. This is because when two ultrasonic sensors are used as in the present embodiment (FIGS. 8 and 9) in which the sensors are disposed at such angles that ultrasonic wave emitting directions and recording sensitivity orientation directions are not parallel to one another, an unseen flowing direction in the blood vessel is specified, and high-precision measurement can be stably performed irrespective of a finger contact position.

Figure 3:
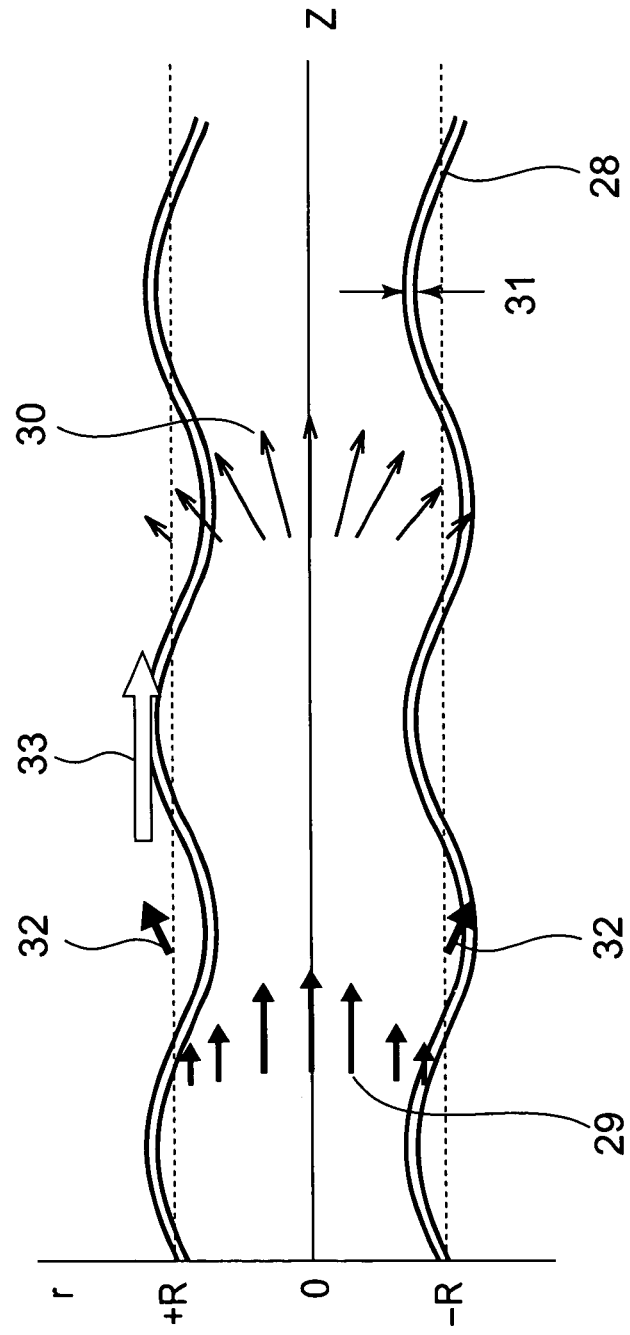
FIG. 3 is a schematic diagram of an artery which pulsates in synchronization with a heartbeat in the present invention.

First, there will be described hereinafter a theoretical background of calculation processing performed by the rheology calculation processing unit 18 in the present invention. FIG. 3 is a schematic diagram of an artery which pulsates in synchronization with heartbeats. On the basis of a pressure distribution 29 in an artery 28, the blood flow generates a blood flow rate distribution 30 in a Z-axis direction which is an axial direction of the artery and radial directions. Needless to say, this pressure distribution 29 is correlated with a blood pressure value. Furthermore, since an artery wall 31 has elasticity, the artery wall 31 causes a vibration displacement in the Z-axis direction and the radial directions. This vibration displacement is a shown pulsatile displacement 32. Furthermore, the pulsatile displacement 32 propagates as a wave through the artery wall in the Z-axis direction together with pulses. This wave is a pulse wave 33. In FIG. 1, it is possible to analytically obtain the pressure distribution 29, the blood flow rate distribution 30, and the pulsatile displacement 32 in accordance with the Navier Stokes equation in hydromechanics and a dynamic equation of the artery wall. That is, assuming that: a heartbeat angular frequency is $\omega$; a pulse wave number is k; an inner diameter of the artery 28 is R; a thickness, Young's modulus, density, and Poisson's ratio of the artery wall 31 are h, E, $\rho_0$, and $\sigma$, respectively; the pressure distribution 29 of the artery 28 is P; an axial-direction rate component of the blood flow rate distribution 30 is V; and the pulsatile displacement of the artery radius direction is $\xi$, P, V, and $\xi$ are determined in accordance with the following equation by use of the Bessel function $J_0$:

$$P = P_0 + P_m J_0(kr) e^{j(\omega t - kz)} \quad \text{Equation (1)}$$

$$V = \sqrt{\frac{R}{\rho E h}} \sqrt{\Phi} \quad \text{Equation (2)}$$

$$P_m \left[ 1 + \frac{J_0\left(j\sqrt{j}\,\alpha\frac{r}{R}\right)}{j_0\left(j\sqrt{j}\,\alpha\right)} \frac{\left[2\frac{1}{\Phi}(1-\sigma^2)-(1-2\sigma)\right]}{(F-2\sigma)} \right] e^{j(\omega t - kz)}$$

$$\xi = P_m \frac{R^2}{Eh} \frac{(F\Phi\sigma - F\sigma^2 + F - \Phi\sigma)}{(F-2\sigma)} e^{j(\omega t - kz)}, \quad \text{Equation (3)}$$

wherein $\phi$ and F are dimensionless functions defined in accordance with the following equation:

$$\Phi = \left(\frac{1}{2}\gamma + \sigma - \frac{1}{4} + \frac{5-4\sigma}{4(1-F)}\right) + \quad \text{Equation (4)}$$

$$\sqrt{\left(-\frac{1}{2}\gamma - \sigma + \frac{1}{4} + \frac{-4\sigma+5}{4F-4}\right)^2 - (1-\sigma^2)\left(\frac{2\gamma+1}{1-F} - 1\right)}$$

$$F = 2 \frac{\sum_{n=0}^{\infty}\left[(-1)^n \frac{1}{{}_n P_n \Gamma(1+n+1)}\left(\frac{j^{\frac{3}{2}}\alpha}{2}\right)^{1+2n}\right]}{j^{\frac{3}{2}}\alpha \sum_{n=0}^{\infty}\left[(-1)^n \frac{1}{{}_n P_n \Gamma(n+1)}\left(\frac{j^{\frac{3}{2}}\alpha}{2}\right)^{2n}\right]} \quad \text{Equation (5)}$$

Moreover, assuming that the artery wall thickness is h, the artery wall density is $\rho_0$, and the artery radius is R, a dimensionless parameter is defined in accordance with the following equation:

$$\gamma = \frac{\rho_o h}{\rho R} \quad \text{Equation (6)}$$

Furthermore, $\alpha$ can be defined as follows by use of the blood kinematic viscosity $\upsilon$, the heartbeat frequency $\omega$, and the radius R:

$$\alpha = R\sqrt{\frac{\omega}{\nu}} \quad \text{Equation (7)}$$

Each of the blood flow rates detected in the embodiments shown in FIGS. 1 and 2 is detected as a waveform having, as an amplitude, a maximum rate component in the blood flow rate distribution V given by the equation (2). This maximum rate component $V_m$ is approximately given by the following equation.

$$V_m = \sqrt{\frac{R}{\rho E h}} \sqrt{\Phi} \quad \text{Equation (8)}$$

$$P_m \left[1 + \frac{K}{J_0(j\sqrt{j}\,\alpha)} \frac{[2(1-\sigma^2)-\Phi(1-2\sigma)]}{\Phi(F-2\sigma)}\right] e^{j(\omega t - kz)},$$

wherein K is not described in detail, but indicates a value which depends on a value of $\alpha$ in a range of 0.65 to 1.

From the above-described analysis results, a phase difference $\delta$ between the maximum rate component $V_m$ and the pulsatile displacement $\xi$ in the axial direction, which periodically fluctuates in synchronization with the heartbeat angular vibration $\omega$ in the artery, is determined in accordance with the equation (9) from the equations (3) and (8).

$$\delta = \arg\left(\sqrt{\Phi} + \frac{K}{J_0(j\sqrt{j}\,\alpha)} \frac{[2(1-\sigma^2)-\Phi(1-2\sigma)]}{\sqrt{\Phi}\,(F-2\sigma)}\right) - \quad \text{Equation (9)}$$

$$\arg\left(\frac{F\Phi\sigma - F\sigma^2 - F - \Phi\sigma}{F-2\sigma}\right)$$

It is found that this phase difference $\delta$ is determined by only dimensionless constants $\alpha$, $\sigma$, and $\gamma$ irrespective of the pressure amplitude $P_m$ in the artery. This is because the dimensionless functions F and Φ appearing in the equation (9) are functions of α, σ, and γ.

Moreover, an amplitude ratio μ of the maximum rate distribution $V_m$ and the pulsatile displacement ξ in the axial direction, which periodically fluctuates in synchronization with the heartbeat angular vibration ω in the artery, is similarly determined in accordance with the (equations (10) and (11) from the equations (3) and (8).

$$\mu = \frac{1}{R}\sqrt{\frac{E\,h}{\rho\,R}}\,\Gamma \qquad \text{Equation (10)}$$

$$\Gamma = \frac{\text{abs}\left[\sqrt{\Phi} + \frac{K}{J_0(j\sqrt{j}\,\alpha)}\frac{[2(1-\sigma^2)-\Phi(1-2\sigma)]}{\sqrt{\Phi}\,(F-2\sigma)}\right]}{\text{abs}\left[\frac{(F\Phi\sigma - F\sigma^2 + F - \Phi\sigma)}{(F-2\sigma)}\right]}, \qquad \text{Equation (11)}$$

wherein Γ denotes a standardized amplitude ratio. It is found that this amplitude ratio μ is determined by the only artery inner diameter R, artery wall thickness h, blood density ρ, artery Young's modulus E, and dimensionless constants α, σ, and γ irrespective of the pressure amplitude $P_m$ in the same manner as in the phase difference δ given by the equation (9).

Figure 4:
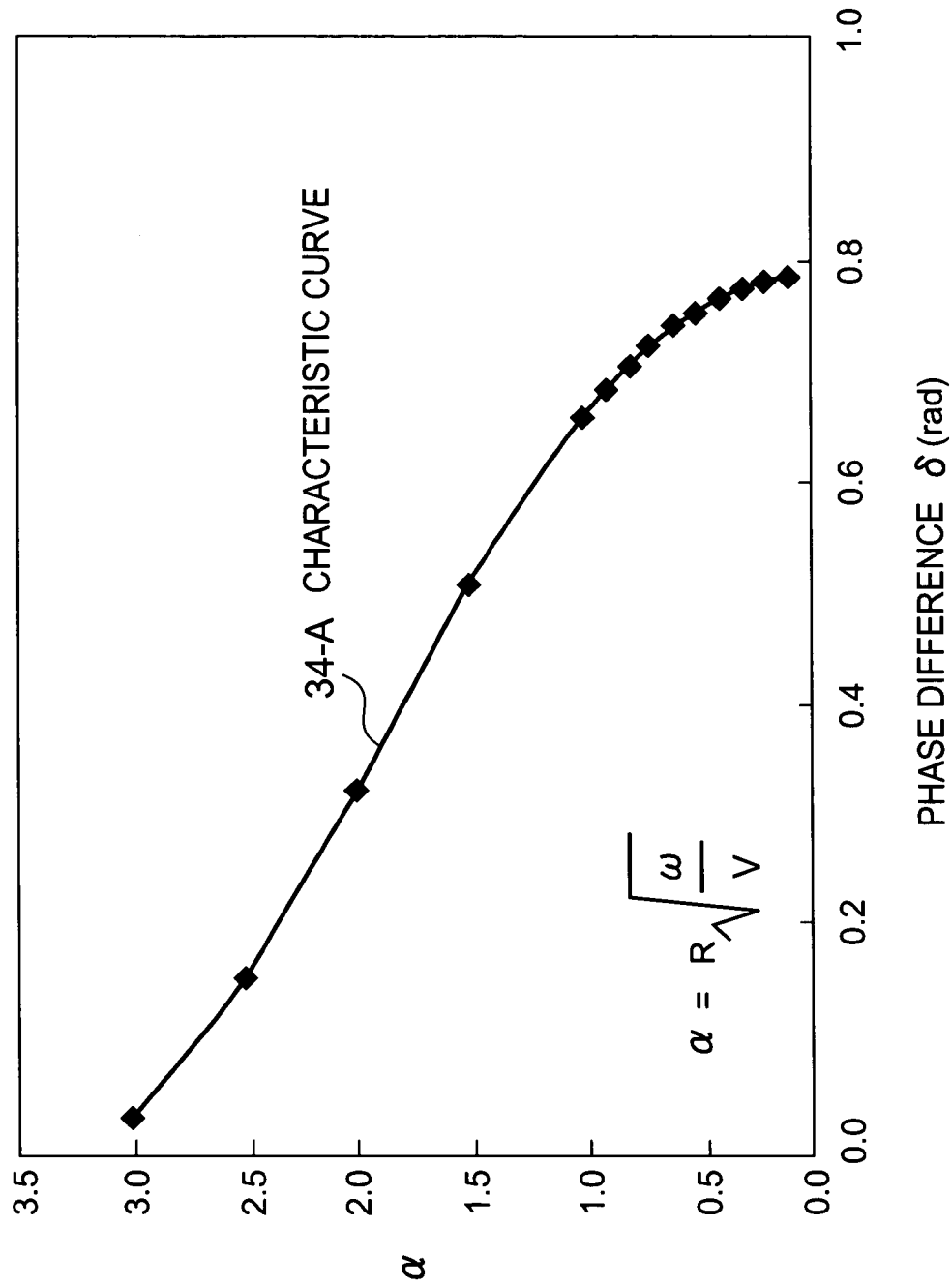
FIG. 4 is a characteristic diagram showing calculation processing for calculating an index of a blood rheology in the present invention.

FIG. 4 is a characteristic diagram obtained by theoretically calculating dependence, on α, of the phase difference δ between the maximum blood flow rate $V_m$ and the pulsatile displacement ξ, calculated in accordance with the equation (9), and is a characteristic diagram showing calculation processing of an index of the blood rheology in the present invention. The ordinate indicates α, and the abscissa indicates the phase difference δ. It is found that a characteristic curve 34-A of this characteristic diagram does not change largely with the following typical values of σ and γ of a living tissue, and is substantially determined by a change of the value of α:

σ=0.4 to 0.6, and γ=0.0 to 0.3.

As defined by the equation (7), α is determined by the heartbeat vibration ω, the blood kinematic viscosity υ, and the artery inner radius R. Therefore, when the phase difference δ, the heartbeat vibration ω, and the artery inner diameter R are measured, the blood kinematic viscosity υ can be detected irrespective of the pressure P in the artery. That is, the blood kinematic viscosity υ can be detected without measuring the blood pressure.

Figure 5:
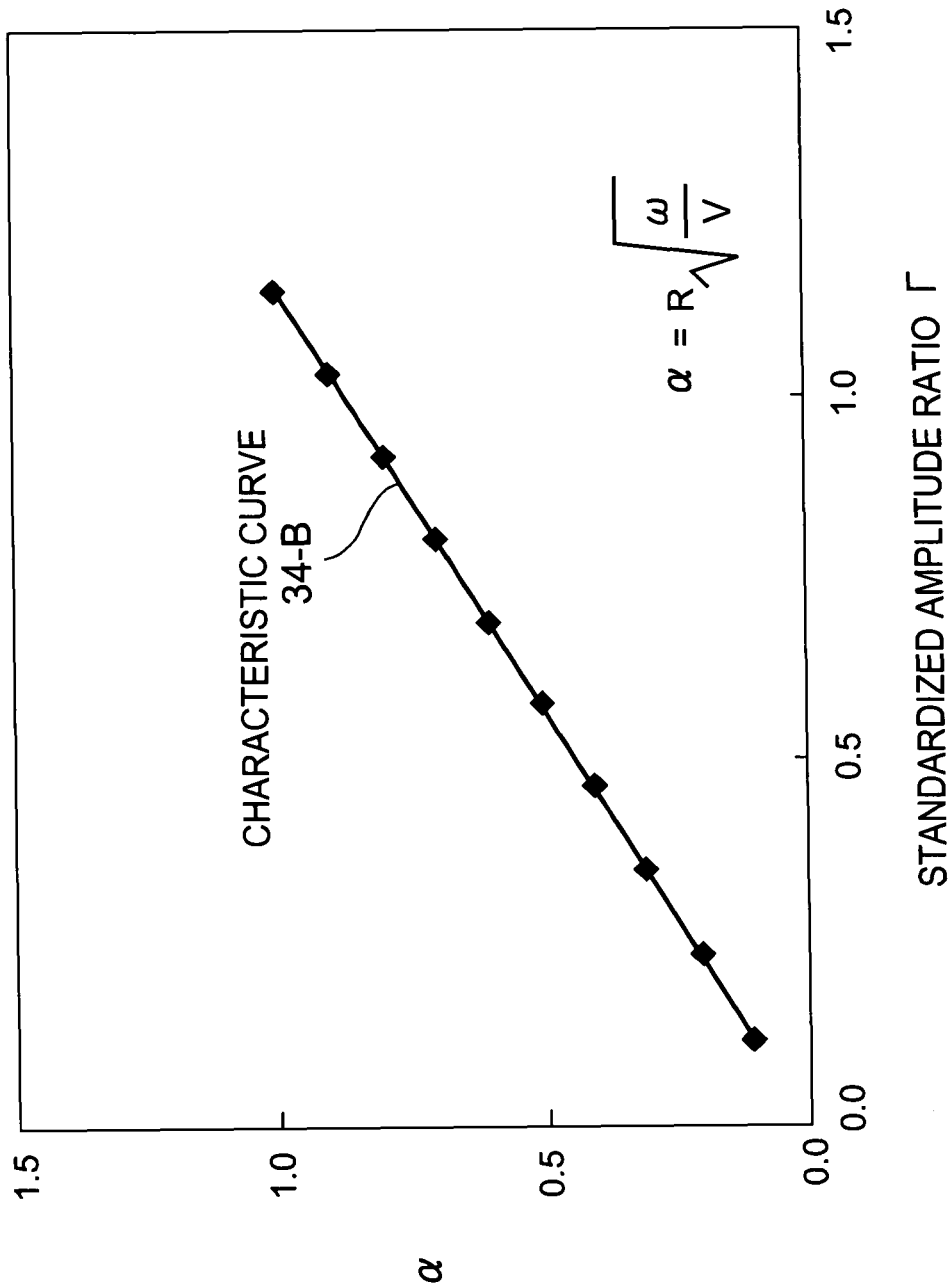
FIG. 5 is a characteristic diagram showing the calculation processing for calculating the index of the blood rheology in the present invention.

FIG. 5 is a characteristic diagram obtained by theoretically calculating a relation between the standardized amplitude ratio Γ of the maximum blood flow rate Vm and the pulsatile displacement ξ calculated by the equation (11) and α defined by the equation (7), and is a characteristic diagram for calculating the index of the blood rheology in the present invention. The ordinate indicates α, and the abscissa indicates the standardized amplitude ratio Γ. It is found that a characteristic curve 34-B of this characteristic diagram does not change largely with the following typical values of σ and γ of the living tissue, and is substantially determined by the change of the value of α:

σ=0.4 to 0.6, and γ=0.0 to 0.3.

As defined by the equation (7), α is determined by the heartbeat vibration ω, the blood kinematic viscosity υ, and the artery inner radius R. Therefore, when the standardized amplitude ratio Γ, the heartbeat vibration ω, the artery inner diameter R, and the artery wall thickness h are measured, the Young's modulus E and the blood density ρ in the living tissue hardly have any individual difference, and are regarded as certain values. Therefore, the blood kinematic viscosity υ can be detected irrespective of the pressure P in the artery. That is, the blood kinematic viscosity υ can be detected without measuring the blood pressure in the same manner as in the phase difference.

Incidentally, in a conventional method of detecting the blood rheology, the maximum blood flow rate $V_m$ calculated in accordance with the equation (2) is divided by the blood pressure value instead of the pressure amplitude $P_m$. The theoretical background of the calculation processing in the present invention has been described above. Moreover, j appearing in the equations (1) to (9) is an imaginary number (square root of −1), and the calculated value is a complex number, but needless to say, an actually significant physical amount is a real part in the same manner as in an alternating current theory of electronic engineering.

Figure 6:
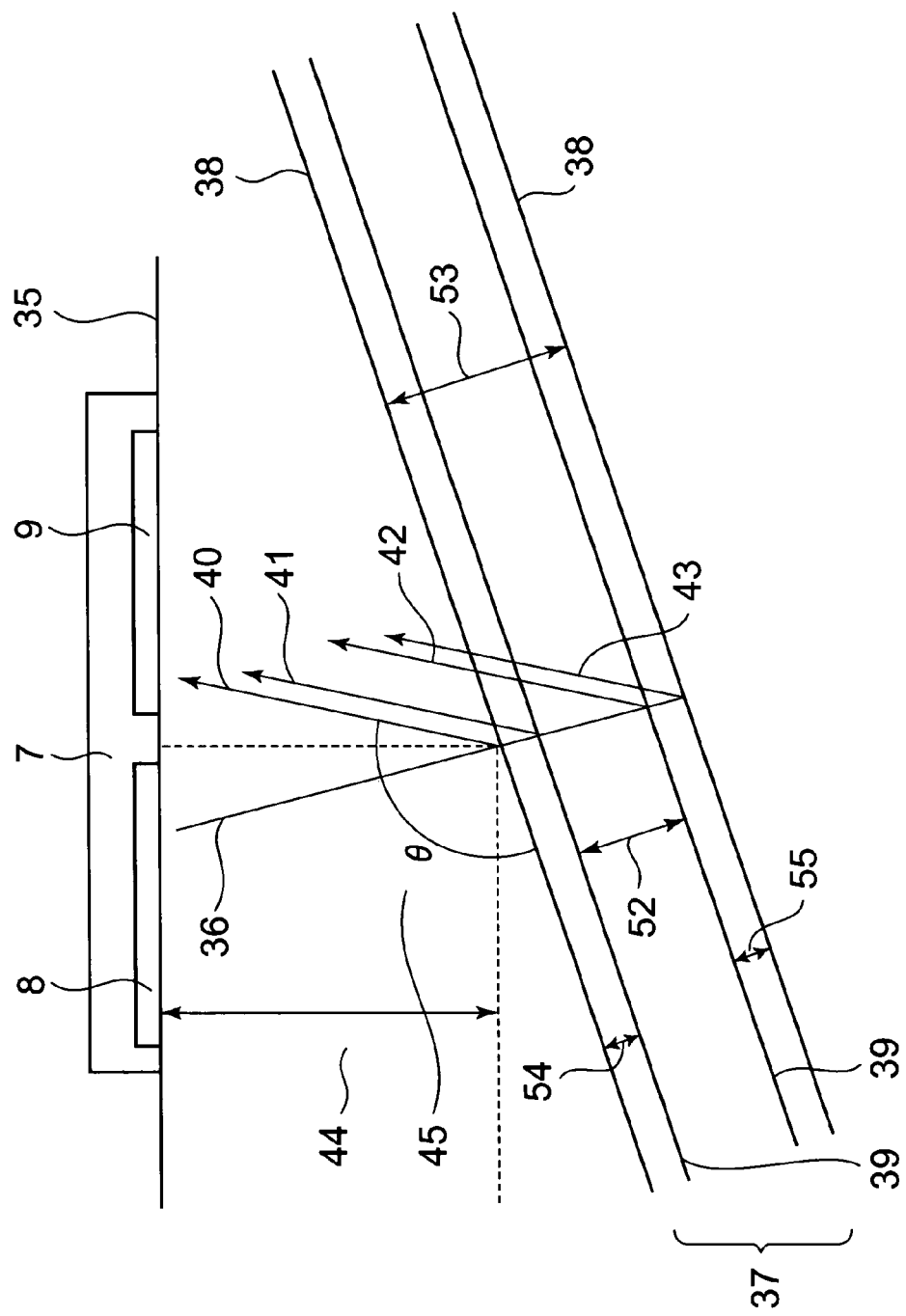
FIG. 6 is a schematic diagram showing the calculation processing for calculating the index of the blood rheology in the present invention.
Figure 7:
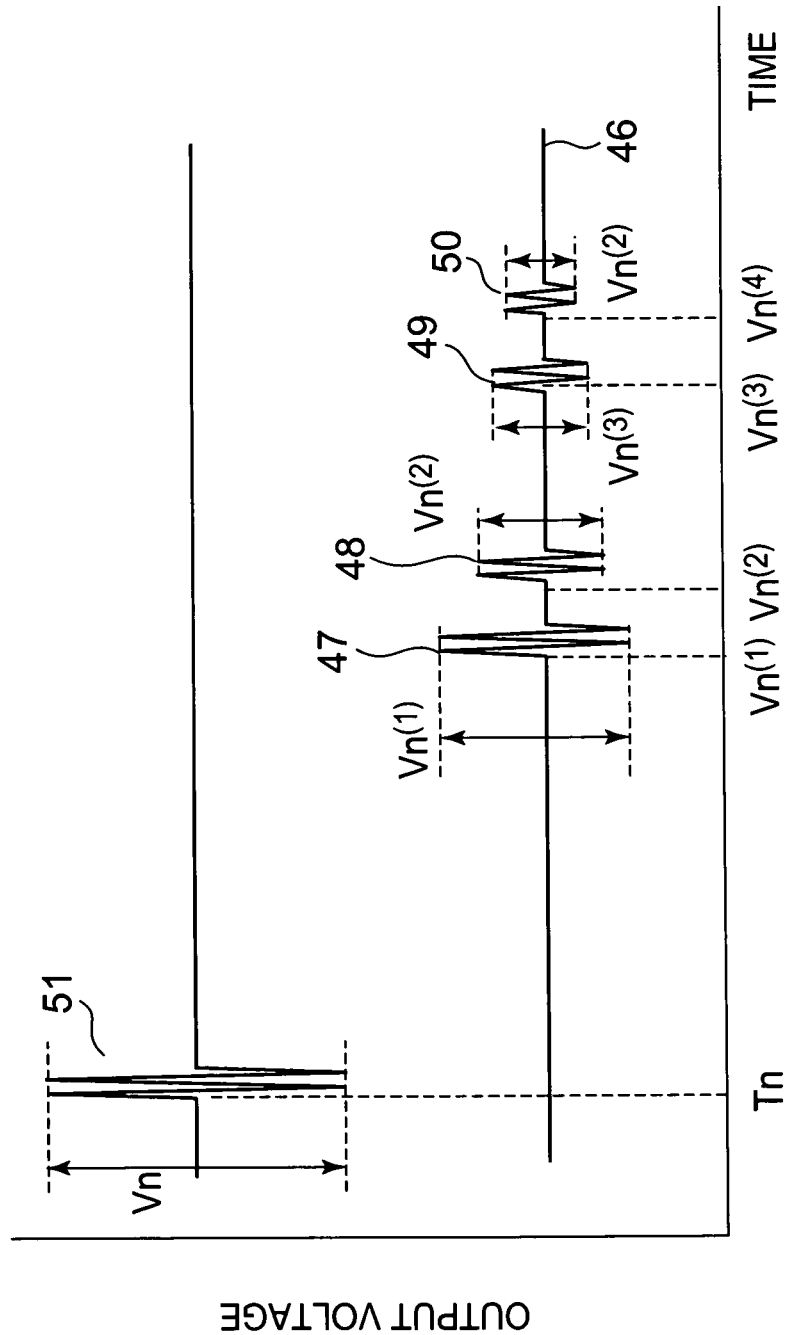
FIG. 7 is a schematic diagram showing the calculation processing for calculating the index of the blood rheology in the present invention.

FIGS. 6 and 7 are principle diagrams showing the calculation processing in the blood vessel information calculation processing unit 17 of the blood rheology measurement device in the present invention. FIG. 6 is a principle diagram in a case where there is used the ultrasonic sensor 7 for measuring the blood vessel information in the blood rheology measurement device of the present invention described with reference to FIG. 1.

The transmitting element 8 of the ultrasonic wave of the ultrasonic sensor 7 attached to skin 35 emits a transmission burst wave 36 to an artery 37. Since the emitted ultrasonic burst wave is reflected by an artery outer wall 38 and an artery inner wall 39 of the artery 37, four types of reflected burst waves are detected by the receiving element 9. These four types of reflected burst waves are a first reflected burst wave 40, a second reflected burst wave 41, a third reflected burst wave 42, and a fourth reflected burst wave 43. Among these four types of reflected burst waves, the first and fourth reflected burst waves 40 and 43 are waves reflected by the artery outer wall 38 of the artery 37, and the second and third reflected burst waves 41 and 42 are waves reflected by the artery inner wall 39. In FIG. 6, a distance between the artery 37 and the skin 35 is an artery distance 44, and an angle between the artery 37 and the skin 35 is an artery angle 45.

These four types of reflected burst waves are detected by the receiving element 9 at different times. FIG. 7 is a characteristic diagram showing output intensities of four types of burst waves observed by the receiving element 9. In FIG. 7, the ordinate indicates signal intensities of a reflected burst signal waveform 46 and a transmitted burst signal waveform 51, and the abscissa indicates time. The transmission burst wave 36 described with reference to FIG. 6 is periodically emitted from the transmitting element 8 into the living body. This emission period ε is sufficiently smaller than a heartbeat period. A time when an n-th transmission burst wave 36 is emitted is a time $T_n$ when the transmitted burst waveform 51 described with reference to FIG. 7 appears. The signal intensity of the transmitted burst waveform 51 is $V_n$. Here, assuming that a first burst wave emission time is 0, the n-th burst wave emission time $T_n$ is as follows by use of the emission period ε:

$$T_n = \varepsilon n\,(1\,2) \qquad \text{Equation (12)}$$

The reflected burst signal waveform 46 reflected by the artery 37 has four peak outputs. That is, they are a first reflected burst signal 47, a second reflected burst signal 48, a third reflected burst signal 49, and a fourth reflected burst signal 50. In this case, the first reflected burst wave 40 corresponds to the first reflected burst signal 47, the second reflected burst wave 41 corresponds to the second reflected burst signal 48, the third reflected burst wave 42 corresponds to the third reflected burst signal 49, and the fourth reflected burst wave 43 corresponds to the fourth reflected burst signal 50. The first to fourth reflected burst signals appear behind the appearance time $T_n$ of the transmitted burst signal waveform 51, and are observed at time $T_n^{(1)}$, $T_n^{(2)}$, $T_n^{(3)}$, and $T_n^{(4)}$, respectively. However, this delay amount is sufficiently smaller than the emission period of the transmission burst wave 36. Signal intensities are $V_n^{(1)}$, $V_n^{(2)}$, $V_n^{(3)}$, and $V_n^{(4)}$, respectively.

The artery 37 described with reference to FIG. 6 pulsates accompanying the periodic motion of the heart. Therefore, the times $T_n^{(1)}$ to $T_n^{(4)}$ when the signal waveforms appear and the signal intensities $V_n^{(1)}$ to $V_n^{(4)}$ periodically change with respect to time. This time period is nothing but the heartbeat period of the living body.

In the blood vessel information calculation processing unit 17 described with reference to FIGS. 1 and 2 in the present invention, the reflected burst signal waveform 46 and the transmitted burst signal waveform 51 described with reference to FIG. 7 are measured at arbitrary times. As waveform information, the times $T_n^{(1)}$ to $T_n^{(4)}$ when the signal waveforms appear and the signal intensities $V_n^{(1)}$ to $V_n^{(4)}$ are measured. Parameters shown in Table 1, that is, delay time differences $\Delta\tau$ and signal intensity ratios are detected from these measured values.

TABLE 1

| | Delay time difference $\Delta\tau$ | Signal intensity ratio |
|---|---|---|
| First reflected burst signal | $\Delta\tau_1(n) = T_n^{(1)} - T_n$ | $a_1(n) = V_n^{(1)}/V_n$ |
| Second reflected burst signal | $\Delta\tau_2(n) = T_n^{(2)} - T_n^{(1)}$ | $a_2(n) = V_n^{(2)}/V_n$ |
| Third reflected burst signal | $\Delta\tau_3(n) = T_n^{(3)} - T_n^{(2)}$ | $a_3(n) = V_n^{(3)}/V_n$ |
| Fourth reflected burst signal | $\Delta\tau_4(n) = T_n^{(4)} - T_n^{(3)}$ | $a_4(n) = V_n^{(4)}/V_n$ |

Numeric values shown in Table 1 are measured every emission of the transmitted burst signal waveform 51. The number of times of emission is a sampling number. The blood vessel shape information and the pulsatile displacement of the artery 37 are detected using the parameters shown in Table 1. There will be described hereinafter calculation processing to detect the blood vessel shape information and the pulsatile displacement.

The blood vessel shape information detected by the blood vessel information calculation processing unit 17 in the present invention are an artery inner diameter 52, an artery outer diameter 53, an artery wall thickness 54, an artery wall thickness 55, and a ratio (artery wall thickness/artery inner diameter) between the artery inner diameter and the artery wall thickness shown in FIG. 6.

The artery radius R in the above-described theoretical equations (1) to (11) is equal to a time average value of the artery inner diameters 52 detected by the blood vessel information calculation processing unit 17 in the present invention. The artery inner diameter 52 periodically changes in synchronization with the heartbeat frequency. The artery inner diameter 52 is proportional to a delay time difference $\Delta\tau_3(n)$ between the second reflected burst signal 48 and the third reflected burst signal 49 shown in FIG. 7. That is, assuming that the artery inner diameter 52 at the n-th emission time of the transmission burst wave 36 is $D_1(n)$, the following equation results.

$$D_1(n) = \frac{1}{2}C\Delta\tau_3(n)\sin\theta \qquad \text{Equation (13)}$$

From the time average value of $D_1(n)$, the artery inner diameter R is as follows:

$$R = \frac{1}{4m}C\sin\theta\sum_{l=0}^{m-1}\Delta\tau_3(l), \qquad \text{Equation (14)}$$

wherein m denotes the sampling number.

Similarly, the artery outer diameter 53 is proportional to a delay time difference between the first reflected burst signal 47 and the fourth reflected burst signal 50 shown in FIG. 7. That is, the artery outer diameter is proportional to a sum of $\Delta\tau_2(n)$, $\Delta\tau_3(n)$, and $\Delta\tau_4(n)$ shown in Table 1. Therefore, assuming that the artery outer diameter 53 at the n-th emission time of the transmission burst wave 36 is $D_2(n)$, the following equation results.

$$D_2(n) = \frac{1}{2}C[\Delta\tau_2(n) + \Delta\tau_3(n) + \Delta\tau_4(n)]\sin\theta \qquad \text{Equation (15)}$$

From the time average value of $D_2(n)$, an average value $D_2$ of the artery outer diameters 53 is as follows:

$$D_2 = \frac{1}{2m}C\left[\sum_{l=0}^{l=m-1}\Delta\tau_2(l) + \sum_{l=0}^{l=m-1}\Delta\tau_3(l) + \sum_{l=0}^{L=m-1}\Delta\tau_4(l)\right]\sin\theta \qquad \text{Equation (16)}$$

Furthermore, the artery wall thickness 54 is proportional to a time average of delay time differences between the first reflected burst signal 47 and the second reflected burst signal 48, and the artery wall thickness 55 is proportional to a time average of delay time differences between the third reflected burst signal 49 and the fourth reflected burst signal 50. That is, assuming that the average value of the artery wall thicknesses 54 is $h_1$, and the average value of the artery wall thicknesses 55 is $h_2$, the values are detected as follows.

$$h_1 = \frac{1}{2m}C\sin\theta\sum_{l=0}^{m-1}\Delta\tau_2(l) \qquad \text{Equation (17)}$$

$$h_2 = \frac{1}{2m}C\sin\theta\sum_{l=0}^{m-1}\Delta\tau_4(l) \qquad \text{Equation (18)}$$

Since $h_1$ is equal to $h_2$, there is not any problem even in a case where either value is adopted as the value h of the artery wall thickness 31. If the values largely differ from each other, there is not any problem even in a case where the average value of $h_1$ and $h_2$ is adopted. That is, the following equation may be established:

$$h = \frac{1}{2}(h_1 + h_2) \qquad \text{Equation (19)}$$

Furthermore, a ratio h/R between the artery inner diameter R and the artery wall thickness h is obtained as follows by use of the equations (14), and (17) to (19):

$$\frac{h}{R} = \frac{h_1}{R} = 2\frac{\sum_{l=0}^{m-1} \Delta\tau_2(l)}{\sum_{l=0}^{m-1} \Delta\tau_3(l)} \qquad \text{Equation (20)}$$

or $$\frac{h}{R} = \frac{h_2}{R} = 2\frac{\sum_{l=0}^{m-1} \Delta\tau_4(l)}{\sum_{l=0}^{m-1} \Delta\tau_3(l)}$$

or $$\frac{h}{R} = \frac{h_1}{2R}(h_1 + h_2) = \frac{\sum_{l=0}^{m-1} \Delta\tau_2(l) + \sum_{l=0}^{m-1} \Delta\tau_4(l)}{\sum_{l=0}^{m-1} \Delta\tau_3(l)}.$$

Next, there will be described calculation processing to detect the pulsatile displacement. The pulsatile displacement is detected from a change amount of the artery inner diameter 52 with elapse of time or a change amount of the artery outer diameter with elapse of time. That is, the amount is detected as follows by use of the equations (13) to (16):

$$\xi_1 = \frac{1}{2}D_1(n) - R; \text{ or} \qquad \text{Equation (21)}$$

$$\xi_2 = \frac{1}{2}D_2(n) - \frac{1}{2}D_2. \qquad \text{Equation (22)}$$

Since $\xi_1$ is usually equal to $\xi_2$, there is not any problem even in a case where either value is adopted as the value $\xi$ of the pulsatile displacement. If the values largely differ from each other, there is not any problem even in a case where the average value of $\xi_1$ and $\xi_2$ is adopted. That is, the following equation may be established:

$$\xi = \frac{1}{2}(\xi_1 + \xi_2) \qquad \text{Equation (23)}$$

As another method, the pulsatile displacement may be determined utilizing a fact that the artery distance 44 shown in FIG. 6 is proportional to a change of the delay time difference $\Delta\tau_1(n)$ with elapse of time, between the appearance time $T_n^{(1)}$ of the first reflected burst signal 47 and the appearance time $T_n$ of the transmitted burst signal waveform 51 shown in Table 1.

As to the actual reflected burst wave in the living body, since the reflected wave from each tissue in the living body exists, there exist many reflected waves other than the reflected waves from the artery shown in FIG. 7. Therefore, it is necessary to detect the reflected wave from the artery from a large number of reflected waves. First, a large characteristic of the reflected wave from the artery lies in that a periodic fluctuation is involved in synchronization with the heartbeat frequency. This periodic fluctuation is observed in not only the delay time difference $\Delta\tau$ but also the amplitude intensity ratios shown in Table 1. Furthermore, among the amplitude intensity ratios, the amplitude intensity ratio of the first reflected burst wave is proportional to a size of an artery outer shape $D_2$.

The blood flow rate measured by the blood rheology measurement device of the present invention is a flow rate of the blood flowing through the artery having a maximum outer diameter (inner diameter) in a portion to be measured. Therefore, signals having the delay time differences and the amplitude intensities synchronized with the heartbeat frequency are detected, and the reflected burst wave having the maximum amplitude intensity ratio is selected from these signals to select the reflected wave from the artery.

Figure 8:
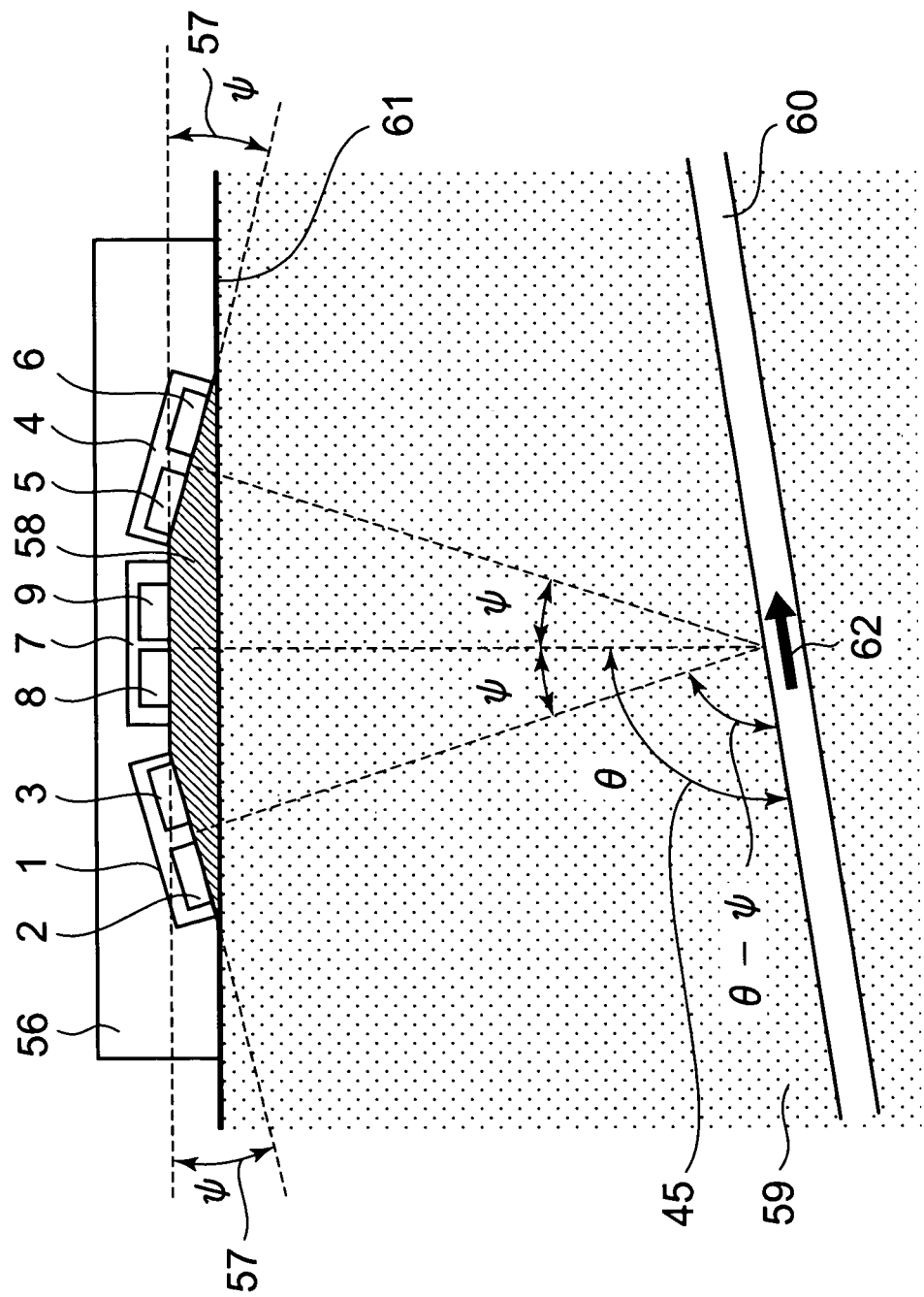
FIG. 8 is a schematic diagram showing a structure of a sensor unit and blood rheology measurement in the present invention.

Next, a size $\theta$ of the artery angle 45 shown in the equations (10) to (18) is detected by the blood flow rate calculation processing unit 16 shown in FIG. 1 as described later. FIG. 8 is a schematic diagram showing a position relation between a structure of a sensor unit of the present invention and the artery in the living body, and is a schematic diagram showing the blood rheology measurement device of the present invention in the embodiment of FIG. 1. A pair of ultrasonic sensors 1 and 4, and an ultrasonic sensor 7 are disposed on the same sensor substrate 56. The pair of ultrasonic sensors are tilted to form a sensor angle 57 so that emitting and receiving directivity directions of a continuous ultrasonic wave are not parallel to one another. A size of the sensor angle 57 is $\psi$. The ultrasonic sensor 7 for transmitting and receiving the burst wave is disposed in an intermediate position between the ultrasonic sensors 1 and 4.

Moreover, the ultrasonic sensors 1 and 4 are connected to the ultrasonic wave circuit 12 shown in FIG. 1. The ultrasonic sensors 1 and 4 transmit continuous ultrasonic waves to an artery 60, and receive reflected continuous ultrasonic waves to a flow of blood flowing through the artery 60. A blood flow rate component is detected from frequency components of the received ultrasonic waves by a blood flow rate calculation processing unit 16. The ultrasonic sensor 7 transmits and receives a burst wave, and pulsatile displacement and blood vessel shape information are detected by a blood vessel information calculation processing unit 17 via a burst detecting circuit 14. As to a transmitting element 2 and a receiving element 3, a transmitting element 5 and a receiving element 6, and a transmitting element 8 and a receiving element 9 constituting the ultrasonic sensors 1, 4 and 7, materials are piezoelectric ceramics.

The sensor substrate 56 is disposed on a living body surface 61 via an acoustic matching layer 58. An angle formed by the artery 60 present in a living tissue 59 and the sensor substrate 56 is an artery angle 45, and its size is $\theta$. The continuous ultrasonic waves transmitted from the ultrasonic sensors 1 and 4 to the artery 60 are reflected by a blood flow 62 in the artery 60, and received as reflected ultrasonic waves involving the Doppler shift (frequency shift) due to the Doppler effect by the receiving elements of the ultrasonic sensors 1 and 4.

The Doppler shift amounts of the received continuous ultrasonic waves are detected by a continuous ultrasonic wave detecting circuit 11 and the blood flow rate calculation processing unit 16. Furthermore, the blood flow rate calculation processing unit 16 determines an artery angle $\theta$ and a blood flow rate V. That is, assuming that the Doppler shift amount observed by the ultrasonic sensor 1 is $\Delta f_1$, the Doppler shift amount observed by the ultrasonic sensor 4 is $\Delta f_2$, and the blood flow rate of the blood flow 62 is V, $\Delta f_1$ and $\Delta f_2$ are obtained as follows:

$$\Delta f_1 = \frac{2V}{C}\cos(\theta - \varphi); \text{ and} \qquad \text{Equation (24)}$$

-continued $$\Delta f_2 = \frac{2V}{C}\cos(\theta + \varphi).\qquad\text{Equation (25)}$$

Therefore, V and θ can be determined using these two equations as simultaneous equations. As a result, sin θ of the equations (10) to (18) can be determined as follows:

$$\sin\theta = \frac{|\Delta f_1 - \Delta f_2|\cos\varphi}{\sqrt{(\Delta f_1 + \Delta f_2)^2\sin^2\varphi + (\Delta f_1 - \Delta f_2)^2\cos^2\varphi}},\qquad\text{Equation (26)}$$

wherein a value of θ is obtained. The value can be substituted into the equation (24) or (25) to detect the blood flow rate V.

Figure 9:
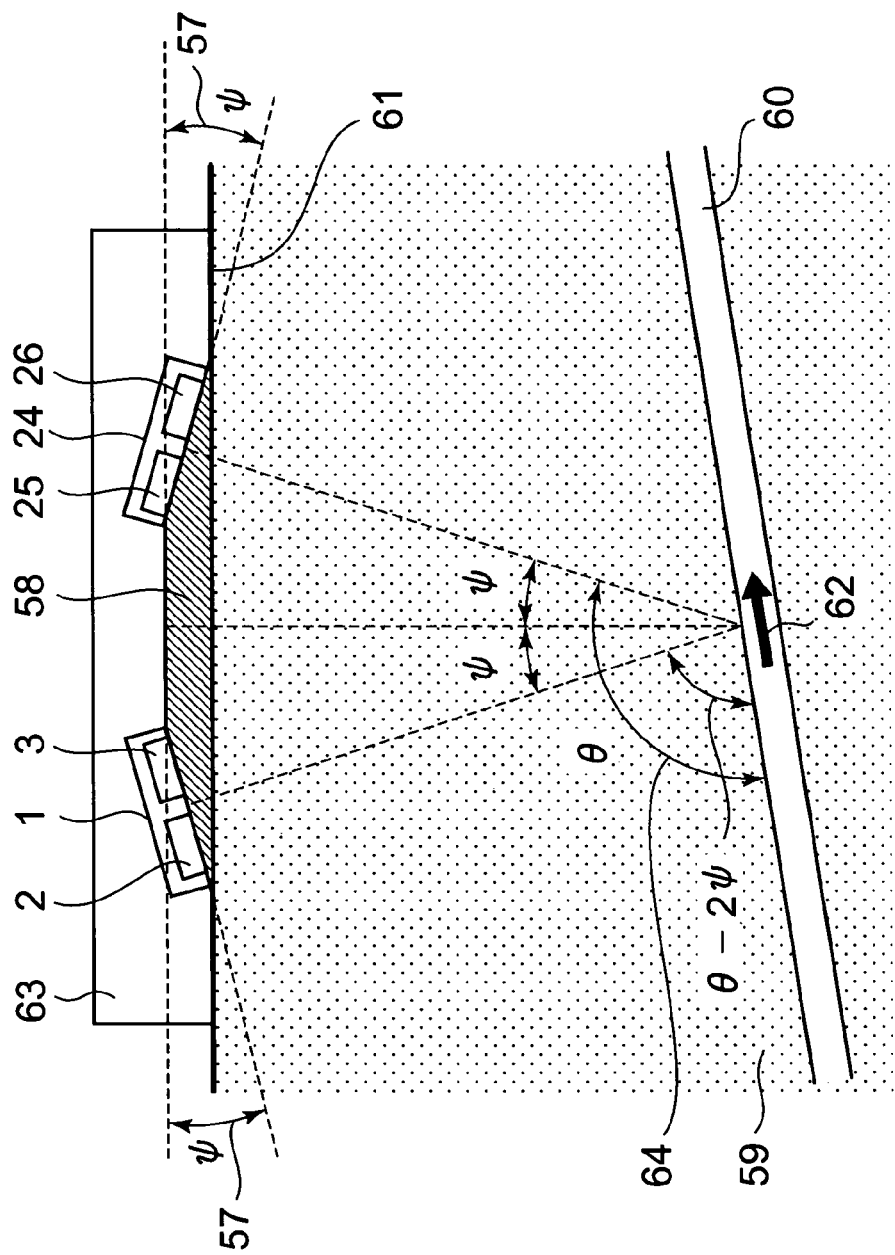
FIG. 9 is a second schematic diagram showing the structure of the sensor unit and the blood rheology measurement in the present invention.

FIG. 9 is a second schematic diagram showing a positional relation between a structure of a sensor unit of the present invention and an artery in a living body, and is a schematic diagram corresponding to the embodiment of FIG. 2 showing a blood rheology measurement device of the present invention. A pair of ultrasonic sensors 1 and 24 are disposed on the same sensor substrate 63. The pair of ultrasonic sensors are tilted to form a sensor angle 57 so that emitting and receiving directivity directions of ultrasonic waves are not parallel to one another in the same manner as in FIG. 8. A size of the sensor angle 57 is ψ. Furthermore, materials of a transmitting element 2 and a receiving element 3, and a transmitting element 25 and a receiving element 26 constituting the ultrasonic sensors 1 and 24 are piezoelectric ceramics.

As described with reference to FIG. 2, in the sensor structure shown in FIG. 9, the transmitting element 25 an dh receiving element 26 constituting the ultrasonic sensor 24 are connected to both of the ultrasonic wave circuit 12 and the ultrasonic burst circuit 15 shown in FIG. 1 via a switch circuit 27. The switch circuit 27 periodically switches the circuit to be connected to the ultrasonic sensor 24 to the ultrasonic wave circuit 12 or the ultrasonic burst circuit 15. That is, the size θ of an artery angle 64 to be obtained can be determined by use of the Doppler shift amount $\Delta f_2$ observed by the ultrasonic sensor 24 and the Doppler shift amount $\Delta f_1$ observed by the ultrasonic sensor 1 as follows.

$$\tan\theta = \frac{\Delta f_1 - \Delta f_2\cos 2\varphi}{\Delta f_2\sin 2\varphi}\qquad\text{Equation (27)}$$

Furthermore, the blood flow rate V is described as follows.

$$V = \frac{1}{2f}C\frac{\sqrt{\Delta f_2^2 + \Delta f_1^2 - 2\Delta f_1\Delta f_2\cos 2\varphi}}{\sin 2\varphi}\qquad\text{Equation (28)}$$

Figure 10:
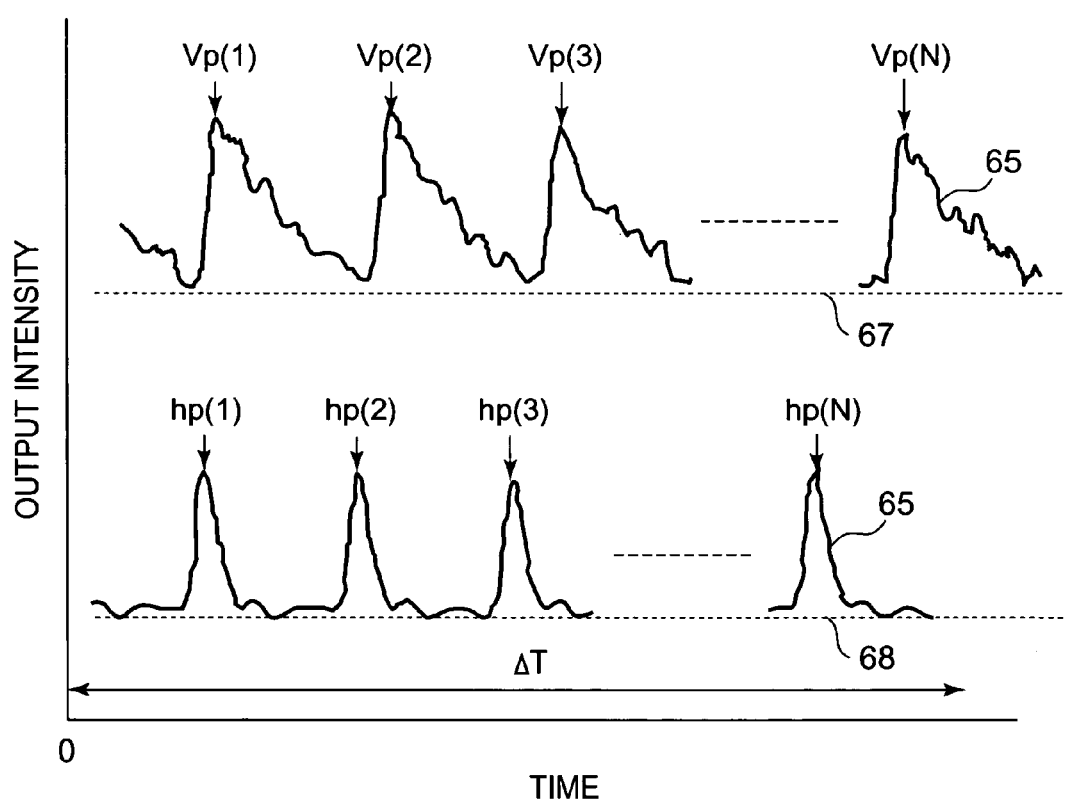
FIG. 10 is an explanatory view showing a blood flow rate waveform and a pulsatile displacement waveform in the present invention.

FIG. 10 is an explanatory view showing a waveform (blood flow rate waveform) 65 of a blood flow rate signal which periodically changes in synchronization with a heartbeat signal calculated and processed in the blood flow rate calculation processing unit 16, and a pulsatile displacement waveform 66 which similarly periodically changes in synchronization with a heartbeat signal calculated and processed in the blood vessel information calculation processing unit 17. The ordinate indicates an output intensity, indicates a rate intensity in the blood flow rate waveform 65, and indicates a detected pulsatile displacement ξ in accordance with the equation (21), (22), or (23) in the pulsatile displacement waveform 66. The abscissa indicates time, and both of the blood flow rate waveform 65 and the pulsatile displacement waveform 66 shown in the drawing have N peak values in a range of a time interval ΔT.

That is, the blood flow rate waveform 65 has N peak values $V_p(1)$ to $V_p(N)$, and the pulsatile displacement waveform 66 has N peak values $\xi_p(1)$ to $\xi_p(N)$. These peak values are measured values from a base line 67 of the blood flow rate waveform 65, and measured values from a base line 68 of the pulsatile displacement waveform 66. Therefore, these peak values are amplitude intensities of both of the waveforms.

Table 2 compiles and shows the peak value $V_p(1)$ of the blood flow rate waveform 65 and an appearance time $\tau_V(n)$, and the peak value $\xi_p(n)$ of the pulsatile displacement waveform 66 and an appearance time $\tau_h(n)$ shown in FIG. 10.

TABLE 2

| Peak number | Blood flow rate waveform | | Pulsatile displacement waveform | |
|---|---|---|---|---|
| | Peak appearance time | Peak value | Peak appearance time | Peak value |
| 1 | $\tau_V(1)$ | $V_P(1)$ | $\tau_h(1)$ | $\xi_P(1)$ |
| 2 | $\tau_V(2)$ | $V_P(2)$ | $\tau_h(2)$ | $\xi_P(2)$ |
| 3 | $\tau_V(3)$ | $V_P(3)$ | $\tau_h(3)$ | $\xi_P(3)$ |
| n | $\tau_V(n)$ | $V_P(n)$ | $\tau_h(n)$ | $\xi_P(n)$ |
| N | $\tau_V(N)$ | $V_P(N)$ | $\tau_h(N)$ | $\xi_P(N)$ |

The N peak values of the blood flow rate waveform 65 shown in Table 2 correspond to the maximum blood flow rate $V_m$ of a blood flow rate distribution given by the equation (2).

Next, there will be described hereinafter the waveform information calculation processing unit 19, the heartbeat frequency calculation processing unit 20, the parameter calculation processing unit 21, and the rheology index calculation processing unit 22 built in the rheology calculation processing unit 18 of the present invention. The waveform information calculation processing unit 19 which is a first calculation processing unit detects the waveform information (peak value) shown in Table 2. As a calculation processing method concerning a waveform in this waveform information calculation processing unit 19, a calculation processing method is adopted in which a peak detecting method or the like using a comparator is used.

Next, the heartbeat frequency calculation processing unit 20 which is a second calculation processing unit obtains a time interval of peak value appearance of the blood flow rate waveform 65 or the pulsatile displacement waveform 66 in the waveform information shown in FIG. 2 in accordance with the following calculation processing equation (1):

$$\Delta\tau(n)=\tau_v(n)-\tau_v(n-1)$$

or $$\Delta\tau(n)=\tau_h(n)-\tau_h(n-1)\qquad\text{Calculation processing equation (1).}$$

Furthermore, a heartbeat frequency F is detected by the following second calculation processing equation (2).

$$F = \frac{N}{\sum_{n=1}^{N}\Delta\tau(n)}\qquad\text{Calculation processing equation (2)}$$

This calculation processing method is a calculation processing method on the basis of the peak value, but may be based on minimum values of the blood flow rate waveform 65 and the pulsatile displacement waveform 66 shown in FIG. 10 without any essential problem.

The parameter calculation processing unit 21 which is a third calculation processing unit built in the rheology calculation processing unit 18 of the present invention detects at least one of a phase difference and an amplitude ratio by means of calculation processing from both of the blood flow rate waveform 65 and the pulsatile displacement waveform 66.

First, detection of the phase difference will be described. In the detection of the phase difference, time differences of N peak appearance times of the blood flow rate waveform 65 and the pulsatile displacement :waveform 66 are obtained in accordance with the following calculation processing equation (3).

$$\Delta \tau_{Vh}(n) = \tau_V(n) - \tau_h(n) \quad \text{Calculation processing equation (3)}$$

Moreover, there is detected a phase difference δ between the blood flow rate waveform 65 and the pulsatile displacement waveform 66 in accordance with the following calculation processing equation (4) by use of an average value of time differences $\Delta \tau_{Vh}(n)$ and the heartbeat frequency F detected by the waveform information calculation processing unit 19.

$$\delta = 2\pi F \frac{\sum_{n=1}^{N} \Delta \tau_{Vh}(n)}{N} \quad \text{Calculation processing equation (4)}$$

Moreover, an amplitude ratio μ is detected as an average value of a ratio $V_p(n)/\xi_p(n)$ of the peak values of the N blood flow rate waveforms 65 and pulsatile displacement waveforms 66 shown in Table 2. That is, the ratio is detected as follows:

$$\mu = \frac{1}{N} \sum_{n=1}^{N} \frac{V_p(n)}{\xi_p(n)} \quad \text{Calculation processing equation (5)}$$

In the above-described calculation processing, the calculation processing concerning the phase difference is a calculation processing method on the basis of the peak value, but may be based on minimum values of the blood flow rate waveform 65 and the pulsatile displacement waveform 66 shown in FIG. 10 without any essential problem.

Furthermore, in the waveform information calculation processing unit 19 of the present embodiment, a general calculation processing method such as the Fourier analysis method or a phased locked loop (PLL) method is adopted as calculation processing means of waveform information. Accordingly, the heartbeat frequency F and the phase difference δ may be detected directly on the basis of the blood flow rate waveform 65 and the pulsatile displacement waveform 66 without any problem, and can be appropriately changed.

In the rheology index calculation processing unit 22 which is a fourth calculation processing device built in the rheology calculation processing unit 18 of the present invention, the kinematic viscosity υ is detected from blood vessel information such as the artery radius R detected by the blood vessel information calculation processing unit 17, the heartbeat frequency F detected by the heartbeat frequency calculation processing unit 20, and the phase difference δ or the amplitude ratio μ between the blood flow rate waveform 65 and the pulsatile displacement waveform 66, detected by the parameter calculation processing unit 21.

There will be described a case where the kinematic viscosity υ of the blood is determined by the phase difference δ between the blood flow rate waveform 65 and the pulsatile displacement waveform 66. In this case, the blood kinematic viscosity υ is determined from the characteristic curve 34-A stored in the rheology index calculation processing unit 22 and shown in FIG. 4, the phase difference δ detected by the parameter calculation processing unit 21 (calculation processing equation (4)), the heartbeat frequency F detected by the heartbeat frequency calculation processing unit 20 (calculation processing equation (2)), and the artery radius R detected by the blood vessel information calculation processing unit 17 (equation (14)). First, the value of α is detected from the stored characteristic curve 34-A and the phase difference δ detected by the parameter calculation processing unit 21. Assuming that the detected value of α is $\alpha_1$, the kinematic viscosity υ of the blood to be obtained is determined in accordance with the following calculation processing equation (6) from the heartbeat frequency F and the artery radius R.

$$v = \frac{2\pi F R^2}{(\alpha_1)^2} \quad \text{Calculation processing equation (6)}$$

FIG. 11 is a characteristic diagram showing a correlation between the kinematic viscosity υ detected using this calculation processing equation (6) and the whole blood passing time T which is an index of the blood rheology by a blood sampling system using a micro channel array. As described above, it is found that the kinematic viscosity υ of the blood detected by the blood rheology measurement device of the present invention and the whole blood passing time T have a high degree of correlation.

Next, there will be described a case where the kinematic viscosity υ of the blood is determined by the amplitude ratio μ between the blood flow rate waveform 65 and the pulsatile displacement waveform 66. In this case, the characteristic curve 34-B shown in FIG. 5, the blood density ρ, and the blood vessel Young's modulus E are stored in the rheology index calculation processing unit 22. Furthermore, the blood kinematic viscosity υ is determined by the amplitude ratio μ detected by the parameter calculation processing unit 21 (calculation processing equation (5)), the heartbeat frequency F detected by the heartbeat frequency calculation processing unit 20 (calculation processing equation (2)), and the artery radius R and h/R detected by the blood vessel information calculation processing unit 17 (equations (14) and (20)).

First, there is detected the standardized amplitude ratio Γ defined in accordance with the equations (10) and (11) from the detected amplitude ratio μ, the artery radius R and h/R, further recorded blood density ρ, and the blood vessel Young's modulus E.

Assuming that this detected standardized amplitude ratio is $\Gamma_0$, $\Gamma_0$ is obtained as follows.

$$\Gamma_0 = \frac{R}{\sqrt{\frac{E}{\rho}\left(\frac{h}{R}\right)}} \mu \quad \text{Calculation processing equation (7)}$$

Furthermore, the value of α is detected using $\Gamma_0$ and the characteristic curve 34-B. Assuming that the detected value of α is $\alpha_2$, the kinematic viscosity υ of the blood to be obtained is determined using the following calculation processing equation (8) from the heartbeat frequency F and the artery radius R.

$$v = \frac{2\pi F R^2}{(\alpha_2)^2} \quad \text{Calculation processing equation (8)}$$

Incidentally, it is found that since the kinematic viscosity υ is calculated from the amplitude ratio, there is hardly an individual difference of the living body in the values of the stored blood density ρ and the blood vessel Young's modulus E, and a detection precision equal to that of the characteristic diagram of FIG. 11 is obtained.

In the present invention, it is possible to measure the blood flow rate in the living body, which has a strong correlation with the blood rheology as the index indicating the fluidity of the body fluid for the medical purpose of maintaining and enhancing the health. In addition, the present invention is usable in measurement to know the activity situation of the living body (human body) and the blood flow condition in each part of the living body.

What is claimed is:

1. A blood rheology measurement device comprising:
a first measurement unit that measures a flow rate of blood flowing through an artery inside of a living body from outside a surface of the living body and that outputs a time varying blood flow rate waveform corresponding to the measured blood flow rate;
a second measurement unit that measures, from outside the surface of the living body, a diameter of the artery and a pulsatile displacement value corresponding to a displacement of the artery in a diameter direction thereof due to expansion and contraction of the artery resulting from a pulsatile motion of the heart, and that outputs the measured artery diameter and a time varying blood vessel pulsatile displacement waveform corresponding to the pulsatile displacement value; and
a rheology calculation processing unit that calculates a blood rheology in the artery on the basis of the time varying blood flow rate waveform, the time varying blood vessel pulsatile displacement waveform, and the measured artery diameter output from the first and second measurement units;
wherein the second measurement unit comprises: a transmitting section that transmits an ultrasonic burst signal to the artery, and a receiving section that receives a plurality of ultrasonic burst signals reflected by inner and outer walls of the artery as a result of the transmitted ultrasonic burst signal, the transmitted and reflected ultrasonic burst signals forming burst signal waveforms that propagate between the surface of the living body and the artery in the living body with delay time differences therebetween; and a blood vessel information calculation processing unit that calculates a delay time difference between one of the received ultrasonic burst signals and another one of the received ultrasonic burst signals to output the measured artery diameter and the time varying blood vessel pulsatile displacement waveform, the time varying blood vessel pulsatile displacement waveform being detected on the basis of a change amount of the artery diameter that is proportional to the calculated delay time difference between the one of the received ultrasonic burst signals and the another one of the received ultrasonic burst signals; and
wherein the rheology calculation processing unit comprises: a heartbeat frequency calculation processing unit that calculates a heartbeat frequency on the basis of the time varying blood flow rate waveform output from the first measurement unit and the time varying blood vessel pulsatile displacement waveform output from the second measurement unit; a parameter calculation processing unit that calculates a phase difference or an amplitude ratio between the time varying blood flow rate waveform and the time varying blood vessel pulsatile displacement waveform on the basis of the respective waveforms; and a rheology index calculation processing unit that calculates a kinematic viscosity of the blood by use of one of the calculated phase difference and amplitude ratio, the measured artery diameter, and the heartbeat frequency.

2. A blood rheology measurement device according to claim 1; wherein the rheology index calculation processing unit has a storage section that stores a characteristic table or a relational equation indicating a correspondence among the kinematic viscosity, the heartbeat frequency, and the measured blood vessel diameter, the rheology index calculation processing unit calculating the kinematic viscosity by use of the characteristic table or the relational equation stored in the storage section.

3. A blood rheology measurement device according to claim 1; wherein the first measurement unit comprises:
a transmitting and receiving section that transmits and receives, respectively, a continuous ultrasonic signal between the surface of the living body and a blood flow of the artery in the living body; and
a blood flow rate calculation processing unit that calculates a Doppler shift signal subjected to a Doppler transition on the basis of the received continuous ultrasonic signal to output the time varying blood flow rate waveform.

4. A blood rheology measurement device according to claim 1; wherein the transmitting and receiving section comprises:
a sensor section including an ultrasonic sensor element that transmits and receives the ultrasonic burst signal with respect to the living body; and
a transmitting and receiving circuit section that drives the sensor section to detect the received ultrasonic wave.

5. A blood rheology measurement device comprising:
a first measurement unit that measures a flow rate of blood flowing through an artery inside of a living body from outside a surface of the living body and that outputs a time varying blood flow rate waveform corresponding to the measured blood flow rate;
a second measurement unit that measures, from outside the surface of the living body, a diameter of the artery and a pulsatile displacement value corresponding to a displacement of the artery in a diameter direction thereof due to expansion and contraction of the artery resulting from a pulsatile motion of the heart, and that outputs the measured artery diameter and a time varying blood vessel pulsatile displacement waveform corresponding to the pulsatile displacement value; and
a rheology calculation processing unit that calculates a blood rheology in the artery on the basis of the time varying blood flow rate waveform, the time varying blood vessel pulsatile displacement waveform, and the measured artery diameter output from the first and second measurement units;
wherein the first measurement unit comprises a first transmitting and receiving section that transmits and receives a continuous ultrasonic signal between the surface of the living body and a blood flow of the artery in the living body, the first transmitting and receiving section comprising a first sensor section including a pair of ultrasonic sensor elements disposed at such an angle that an emission direction of the ultrasonic wave and a directivity direction of a receiving sensitivity are not parallel to each other;

wherein the second measurement unit comprises: a second transmitting section that transmits an ultrasonic burst signal to the artery, and a second receiving section that receives a plurality of ultrasonic burst signals reflected by inner and outer walls of the artery as a result of the transmitted ultrasonic burst signal, the transmitted and reflected ultrasonic burst signals forming burst signal waveforms that propagate between the surface of the living body and the artery in the living body with delay time differences therebetween, and the second transmitting and receiving sections forming a second sensor section including an ultrasonic sensor element that transmits and receives the ultrasonic burst signals with respect to the living body; and a blood vessel information calculation processing unit that calculates a delay time difference between one of the received ultrasonic burst signals and another one of the received ultrasonic burst signals to output the measured artery diameter and the time varying blood vessel pulsatile displacement waveform, the time varying blood vessel pulsatile displacement waveform being detected on the basis of a change amount of the artery diameter that is proportional to the calculated delay time difference between the one of the received ultrasonic burst signals and the another one of the received ultrasonic burst signal; and wherein the rheology calculation processing unit comprises: a heartbeat frequency calculation processing unit that calculates a heartbeat frequency on the basis of the time varying blood flow rate waveform output from the first measurement unit and the time varying blood vessel pulsatile displacement waveform output from the second measurement unit; a parameter calculation processing unit that calculates a phase difference or an amplitude ratio between the time varying blood flow rate waveform and the time varying blood vessel pulsatile displacement waveform on the basis of the respective waveforms; and a rheology index calculation processing unit that calculates a kinematic viscosity of the blood by use of one of the calculated phase difference and amplitude ratio, the measured artery diameter, and the heartbeat frequency.

6. A blood rheology measurement device according to claim 5; wherein the first and second sensor sections are disposed on a common substrate.

7. A blood rheology measurement device according to claim 1; wherein the transmitting and receiving section of the second measurement unit comprises an ultrasonic sensor having a transmitting element and a receiving element; and wherein the second measurement unit further comprises a burst generation circuit that generates and outputs an electric burst signal to the transmitting element for driving the transmitting element to convert the electric burst signal into the ultrasonic burst signal and to transmit the ultrasonic burst signal between the surface of the living body and the artery in the living body.

8. A blood rheology measurement device according to claim 7; wherein the receiving element of the ultrasonic sensor receives the reflected ultrasonic burst signals and converts the reflected ultrasonic burst signals into electric signals.

9. A blood rheology measurement device according to claim 8; wherein the second measurement unit further comprises a burst detecting circuit that detects as electric signals from the receiving element the burst ultrasonic signals reflected by the inner and outer walls of the artery in the living body.

10. A blood rheology measurement device according to claim 9; wherein the blood vessel information calculation processing unit receives the burst ultrasonic signals detected by the burst detecting circuit.

11. A blood rheology measurement device according to claim 5; wherein the ultrasonic sensor element of the second sensor section comprises a transmitting element and a receiving element; and wherein the second measurement unit further comprises a burst generation circuit that generates and outputs an electric burst signal to the transmitting element for driving the transmitting element to convert the electric burst signal into the ultrasonic burst signal and to transmit the ultrasonic burst signal between the surface of the living body and the artery in the living body.

12. A blood rheology measurement device according to claim 11; wherein the receiving element of the second sensor section receives the reflected ultrasonic burst signals and converts the reflected ultrasonic burst signals into electric signals.

13. A blood rheology measurement device according to claim 12; wherein the second measurement unit further comprises a burst detecting circuit that detects as electric from the receiving element the burst ultrasonic signals reflected by the inner and outer walls of the artery in the living body.

14. A blood rheology measurement device according to claim 13; wherein the blood vessel information calculation processing unit receives the burst ultrasonic signals detected by the burst detecting circuit.

* * * * *